(12) United States Patent
Böhm et al.

(10) Patent No.: US 7,504,533 B2
(45) Date of Patent: Mar. 17, 2009

(54) PROCESS FOR THE PRODUCTION OF ISOCYANATES

(75) Inventors: Matthias Böhm, Leverkusen (DE); Wolfgang Lorenz, Dormagen (DE); Bill L. Brady, Jr., Houston, TX (US); Donald L. Pferdehirt, The Woodlands, TX (US)

(73) Assignees: Bayer MaterialScience LLC, Pittsburgh, PA (US); Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/409,940

(22) Filed: Apr. 24, 2006

(65) Prior Publication Data

US 2007/0249859 A1    Oct. 25, 2007

(51) Int. Cl.
*C07C 263/00* (2006.01)
*C07C 249/00* (2006.01)
(52) U.S. Cl. .................... 560/348; 560/352
(58) Field of Classification Search ............... None
See application file for complete search history.

(56) References Cited

U.S. PATENT DOCUMENTS

| | | | | |
|---|---|---|---|---|
| 2,764,607 | A | * 9/1956 | Edwards et al. | 558/281 |
| 3,142,535 | A | * 7/1964 | Christoph, Jr. | 423/488 |
| 3,211,776 | A | 10/1965 | Stephens | 260/463 |
| 3,226,410 | A | 12/1965 | Hettich et al. | 260/453 |
| 3,381,025 | A | * 4/1968 | Mitsumori et al. | 560/347 |
| 3,544,611 | A | * 12/1970 | Alheritiere et al. | 560/347 |
| 3,574,695 | A | * 4/1971 | Grant, Jr. et al. | 560/347 |
| 3,734,293 | A | 5/1973 | Biskis | 210/185 |
| 3,839,847 | A | 10/1974 | Banikiotes et al. | 95/96 |
| 4,251,457 | A | * 2/1981 | Kondratenko et al. | 562/856 |
| 4,421,530 | A | * 12/1983 | Dalton et al. | 95/99 |
| 4,422,976 | A | * 12/1983 | Yamamoto et al. | 560/347 |
| 4,764,308 | A | 8/1988 | Sauer et al. | 260/544 K |

(Continued)

FOREIGN PATENT DOCUMENTS

DE    30 00 524 A1    7/1981

(Continued)

OTHER PUBLICATIONS

Ullmann's Encyclopedia of Industrial Chemistry, $3^{rd}$ Edition vol. 13, (Date unavailable), pp. 493-500, "Phosgen".

(Continued)

*Primary Examiner*—Karl J Puttlitz
(74) *Attorney, Agent, or Firm*—Lyndanne M. Whalen

(57) ABSTRACT

Isocyanates are produced by a) reacting at least one amine with phosgene, optionally in the presence of a solvent to produce the corresponding isocyanate and a stream containing hydrogen chloride, phosgene and optionally solvent, low-boiling compounds and inert substances is obtained, b) separating the stream containing hydrogen chloride, phosgene and optionally solvent, low-boiling compounds and inert substances in an at least two-stage sequence of absorption steps that includes (1) at least one isothermal absorption step and (2) at least one adiabatic absorption step, to obtain (i) a hydrogen chloride stream containing phosgene in concentrations of at most 0.5 wt. % (based on the weight of the hydrogen chloride stream) and (ii) a liquid phosgene stream, and c) recycling the liquid phosgene stream (ii) to the reaction of amine with phosgene.

13 Claims, 4 Drawing Sheets

U.S. PATENT DOCUMENTS

| | | | | |
|---|---|---|---|---|
| 4,876,380 | A | * 10/1989 | Chen et al. | 560/352 |
| 5,449,818 | A | 9/1995 | Biskup et al. | 560/347 |
| 5,693,853 | A | 12/1997 | Abrahamsson | 560/347 |
| 5,756,063 | A | * 5/1998 | Nuernberg et al. | 423/488 |
| 6,010,612 | A | 1/2000 | Freire et al. | 205/551 |
| 6,149,782 | A | 11/2000 | Allen et al. | 204/290.14 |
| 6,358,381 | B1 | 3/2002 | Allen et al. | 204/283 |
| 6,402,930 | B1 | 6/2002 | Allen et al. | 205/625 |
| 6,479,690 | B1 * | 11/2002 | Garel et al. | 558/280 |
| 6,719,957 | B2 | 4/2004 | Brady, Jr. et al. | 423/488 |
| 6,800,781 | B2 | 10/2004 | Herold et al. | 560/347 |
| 6,916,953 | B2 | 7/2005 | Walsdorff et al. | 560/341 |
| 2002/0123644 | A1 | 9/2002 | Kitai et al. | 560/330 |
| 2004/0024244 | A1 | 2/2004 | Walsdorff et al. | 560/347 |
| 2005/0118088 | A1 | 6/2005 | Olbert et al. | 423/416 |
| 2006/0025556 | A1 * | 2/2006 | Koch et al. | 528/44 |
| 2006/0123842 | A1 * | 6/2006 | Sohn et al. | 62/617 |

FOREIGN PATENT DOCUMENTS

| | | |
|---|---|---|
| DE | 102 60 084 A1 | 7/2004 |
| GB | 737 442 | 9/1955 |
| GB | 827376 | 2/1960 |
| GB | 1077031 | 7/1967 |
| JP | 9-208589 | 8/1997 |
| RU | 1811161 A1 | 5/1995 |

OTHER PUBLICATIONS

Applied Catalysis A: General 221 (month unavailable) 2001, pp. 303-335, Gerhard Wegener et al, "Trends in industrial catalysis in the polyurethane industry" 12th International Forum Electrolysis in Chemical Industry—Clean and Efficient Processing.

Electrochemical Technology for Synthesis, Separations, Recycle and Environmental Improvements, Oct. 11-15, 1998, Dennie Turin Mah, Chlorine Regeneration (Creg) from Anhydrous Hydrogen Chloride.

Ullmann's Encyclopedia of Industrial Chemistry, 5th Edition, vol. A 19, (month unavailable) 1991, pp. 405-411, Robert A. Smiley, "Phenylene- and Toluenediamines".

Polyurethane Handbook, G. Oertel (Ed), 2nd Edition, (month unavailable) 1993, pp. 73-85, Dr. K. Schauerte et al, "Isocyanates".

* cited by examiner

PROCESS FOR THE PRODUCTION OF ISOCYANATES

BACKGROUND OF THE INVENTION

The present invention relates to a process for the production of isocyanates in which the vapor mixture formed when phosgene and amine are reacted is subjected to at least one isothermal absorption treatment and at least one adiabatic absorption treatment.

The production of isocyanates is well known in the prior art. As a rule, phosgene is used in a stoichiometric excess with respect to the amine or a mixture of two or more amines. Processes for the production of organic isocyanates from primary amines and phosgene are described in the literature, for example in Ullmann's Encyclopedia of Industrial Chemistry, $5^{th}$ Edition, Vol. A 19 p. 390 ff., VCH Verlagsgesellschaft mbH, Weinheim, 1991 and G. Oertel (Ed.) Polyurethane Handbook, $2^{nd}$ Edition, Hanser Verlag, Munich, 1993, p. 60 ff. as well as G. Wegener et al. Applied Catalysis A: General 221 (2001), p. 303-335, Elsevier Science B.V.

The synthesis of the phosgene used in the amine phosgenation is well known and is described, for example, in Ullmann's Encyclopedia of Industrial Chemistry, $3^{rd}$ Edition, Vol. 13, pp. 494-500. Other processes for the production of phosgene are described, for example, in U.S. Pat. No. 4,764,308 and WO 03/072237. On an industrial scale, phosgene is mainly produced by reacting carbon monoxide with chlorine, preferably on activated charcoal as catalyst. The highly exothermic gaseous phase reaction is carried out at temperatures of at least 250° C. to at most 600° C., as a rule in shell-and-tube reactors. The heat of reaction may be dissipated in various ways, for example, by means of a liquid heat exchange medium, as described, for example, in WO 03/072237, or by hot cooling via a secondary cooling circuit with simultaneous utilization of the heat of reaction in order to generate steam, as disclosed, for example, in U.S. Pat. No. 4,764,308.

In the amine phosgenation, unreacted phosgene mostly occurs at least in part in gaseous form together with the released hydrogen chloride. Phosgene and hydrogen chloride fractions still contained in the liquid isocyanate-carrying product stream are separated during the course of the isocyanate working-up stage. As a rule, this product stream can still contain fractions of solvent, inert gases, such as for example nitrogen and carbon monoxide, and secondary products of the phosgene synthesis, such as carbon dioxide and possibly entrained isocyanate. In order to operate the process for the production of isocyanates as economically as possible, it is essential to recover the excess phosgene with losses as small as possible and recycle it to the phosgenation process. It is also necessary to separate the stoichiometrically occurring hydrogen chloride gas and use it. Suitable uses for the hydrogen chloride are determined on the basis of the purity requirements on the hydrogen chloride for any given application.

Possible uses for hydrogen chloride include marketing the aqueous solution (hydrochloric acid) or using hydrochloric acid in other industrial or chemical processes. One of the most common possible ways of using gaseous hydrogen chloride is for the oxychlorination of ethylene with hydrogen chloride to form ethylene dichloride. Recycling processes for the hydrogen chloride and the return of the chlorine and/or hydrogen to the production process in which the hydrogen chloride is formed are also among the preferred procedures. These recycling processes include the catalytic oxidation of hydrogen chloride, for example according to the Deacon process, the electrolysis of gaseous hydrogen chloride, as well as the electrolysis of an aqueous solution of hydrogen chloride (hydrochloric acid). WO-A-04/14845 discloses a process for the catalytic oxidation according to the Deacon process, and WO-A-97/24320 discloses a process for the gas phase electrolysis of hydrogen chloride. A review of electrochemical recycling processes is given in the article "Chlorine Regeneration from Anhydrous Hydrogen" by Denne Turin Mah, published in "$12^{th}$ International Forum Electrolysis in Chemical Industry—Clean and Efficient Processing Electrochemical Technology for Synthesis, Separation, Recycle and Environmental Improvement", Oct. 11-15, 1998, Sheraton Sand Key, Clearwater Beach, Fla.

The electrochemical oxidation of an aqueous solution of hydrogen chloride (hydrochloric acid) using a gas diffusion electrode as cathode is described in WO-A-00/73538 and WO-A-02/18675.

In the electrolysis of aqueous hydrogen chloride by the diaphragm or membrane process, hydrochloric acid is used as electrolyte in the anode space as well as in the cathode space. In the electrolysis, chlorine is produced at the anode and hydrogen is produced at the cathode.

The aforementioned possibilities of using hydrogen chloride impose certain purity requirements and thus involve expenditure and equipment on purification after separating the majority of the other components in the gaseous stream containing phosgene and hydrogen chloride. The catalytic hydrogen chloride oxidation by the Deacon process is carried out with a catalyst that requires the preliminary purification of the hydrogen chloride gas from a phosgenation process by means of absorption on a purification bed, or the catalytic combustion of solvent residues contained in the hydrogen chloride (WO-A-04/014845). In the gas phase electrolysis of hydrogen chloride by the so-called solid electrolyte systems according to WO-A-97/24320, a contamination of the ion exchange membrane or of the catalytically active material is unallowable in order to avoid having to replace the units. In the electrochemical oxidation of an aqueous solution of hydrogen chloride using a gas diffusion electrode as cathode, it is suggested in WO-A-02/18675 that the hydrogen chloride (hydrochloric acid) be purified by means of activated charcoal and, if necessary, additionally by means of an ion exchange resin. For the use of hydrogen chloride gas in oxychlorination, a two-stage condensation may be used to separate interfering impurities, such as solvent residues (U.S. Pat. No. 6,719,957).

An aqueous solution of hydrogen chloride (hydrochloric acid) for use in the foodstuffs industry must have a correspondingly high degree of purity, which can be achieved by an adsorptive post-purification on a bed of activated charcoal, as known from the prior art.

The treatment of the phosgene-containing and hydrogen chloride-containing substance streams from the isocyanate production according to the prior art is described hereinafter. The general aim is to isolate the substance streams containing phosgene and hydrogen chloride with secondary components contained therein, such as solvent, in the required purity as economically as possible in order to be able to reuse phosgene in the amine phosgenation and pass the hydrogen chloride to a suitable utilization stage. The processes of condensation, partial condensation, washing/scrubbing, absorption, adsorption and distillation are normally employed for this purpose.

A partial condensation of phosgene from the process gas may be achieved under high pressure, for example at a pressure between 10 and 50 bar, in an energy-efficient manner by means of cooling water, though for exploitation on an industrial scale the stringent safety measures as regards a leakage involving escape of phosgene have to be taken into account, as described in DE-A-3212510.

The phosgenation reaction and working-up of the gas phase under elevated pressure is also described in U.S. Pat. No. 3,544,611. In a pressure range of from 10 to 50 bar, the process gas is cooled with water in order to condense a large part of the phosgene that is used in stoichiometric excess. A further depletion of phosgene in the hydrogen chloride stream requires the use of cooling agents. In this case, the economic advantage of the amine phosgenation with working-up of the process gas at elevated pressure is also reflected in the saving of energy for cooling the phosgene condensation. An alternative is described in U.S. Pat. No. 3,544,611 in which hydrogen chloride is condensed from the process gas stream at 33 bar and at a coolant temperature of −20° C. In this case, phosgene is condensed by cooling with water and separating in a preliminary stage. The respective purities required of the two components is achieved by a distillation/stripping column between the two condensation stages.

In DE-A-10260084 reference is made to U.S. Pat. No. 3,544,611 in connection with an increased potential hazard in the event of a leakage due to this pressurized procedure. It is also noted that in the described processes there is an undesirably high concentration of hydrogen chloride in the phosgene used for the phosgenation, and phosgene is also lost with the hydrogen chloride stream (first variant). In the second variant, apart from the comments on the already-mentioned potential hazard, reference is also made to the energetically unfavorable hydrogen chloride liquefaction at low temperatures and high pressures. For further utilization, the hydrogen chloride must then be evaporated, which again uses energy.

In the process disclosed in GB-A-827376, an amine phosgenation is carried out at a pressure of ca. 3 bar. After completion of the reaction, excess phosgene and hydrogen chloride that are formed are separated overhead in a column at elevated temperature. Phosgene is condensed out from the gaseous phase, and the hydrogen chloride is flashed (expanded) and removed. However, high residual amounts of phosgene in the hydrogen chloride as well as undesirably high hydrogen chloride contents in the recovered phosgene can be expected with such a simple separation.

Amine phosgenation in chlorobenzene to form TDI and MDI is described in U.S. Pat. No. 3,3812,025. After completion of the reaction, solvent together with phosgene and hydrogen chloride are distilled off, chlorobenzene and phosgene are then condensed and recycled to the phosgenation, and hydrogen chloride containing considerable residual amounts of phosgene is passed through an absorber to eliminate the phosgene. In this case too the phosgene/hydrogen chloride separation is incomplete in both streams, so that phosgene losses occur through hydrogen chloride and undesirably high hydrogen chloride fractions are contained in the phosgene, which promote a disadvantageous amine hydrochloride formation in the phosgenation.

The amine phosgenation to isocyanate combined with working-up disclosed in SU-A-1811161 is described in DE-A-10260084. In DE-A-10260084, it is also reported that phosgene is absorbed in gaseous form in the solvent chlorobenzene without prior condensation. After the phosgenation reaction, hydrogen chloride, phosgene and to some extent solvent are separated as gaseous phase. After partial condensation, the gaseous phase is passed to an absorber, the liquid phase is led into a stripping column in which hydrogen chloride and phosgene are separated overhead, and is partially condensed and likewise passed to the absorber. A solution of ca. 70 wt. % of phosgene in chlorobenzene is formed in the absorber. The gaseous hydrogen chloride stream from the absorber head still contains ca. 4% of phosgene and is passed to a further treatment stage. According to DE-A-10260084, the solution of phosgene in chlorobenzene also still contains relatively large amounts of hydrogen chloride due to the chlorobenzene wash at low temperature. According to the details given in DE-A-10260084, hydrogen chloride and phosgene after their separation are still mutually contaminated to such an extent that, as already described, hydrogen chloride cannot be passed without further working-up to one of the conventional utilization stages and the phosgene solution that is obtained is uneconomical for the phosgenation process.

In EP-A-0570799, which is a publication relating to amine phosgenation in the gaseous phase, reference is made to the separation in a manner known per se of excess phosgene after condensation of the isocyanate that is formed. This may be achieved by means of a cold trap, absorption in an inert solvent (e.g., chlorobenzene or dichlorobenzene) maintained at a temperature of −10° C. to 8° C., or by adsorption and hydrolysis on activated charcoal. The last variant does not appear economically feasible for large-scale implementation. The hydrogen chloride gas passing through the phosgene recovery stage can be recycled in a manner known per se to recover the chlorine required for the phosgene synthesis.

A continuous two-stage amine phosgenation process in the liquid phase is described in U.S. Pat. No. 3,226,410. A phosgene solution is admixed in a stoichiometric excess of an amine solution in a tubular reactor at temperatures of up to 90° C. The second stage takes place in a boiler at 110° to 135° C. The gaseous phase, composed of phosgene, hydrogen chloride and solvent fractions, is removed overhead from the second stage, condensed in a two-stage process, and passed to the phosgene solution vessel. Non-condensable fractions pass into an absorption column, where phosgene still contained in the gas stream is absorbed by means of distilled-off solvent from the liquid phase of the phosgenation and is passed to the phosgene solution vessel. Non-absorbed fractions from the absorption column which for the most part are hydrogen chloride gas, are fed to an HCl absorber operated with water, in which aqueous hydrochloric acid is formed.

Apart from the isocyanate production, a phosgene/hydrogen chloride separation is also necessary in the phosgenation of alcohols to form chloroformates. In accordance with the process disclosed in DE-A-69820078, this takes place at high pressures in a column connected downstream of the reactor. The reactor pressure ranges from 2 to 60 bar, preferably 6 to 40 bar. When using high pressure in the phosgene/hydrogen chloride separation, it is pointed out that, from the economic aspect, the condensers no longer have to be operated at low temperatures. In DE-A-3000524 and U.S. Pat. No. 3,211,776, reference is simply made to a blowing-off of excess phosgene in the working-up after the chloroformate formation from alcohol, phosgene and catalyst.

A chemical separation of hydrogen chloride and phosgene is less significant for the industrial production of isocyanate because of the extensive use of, for example, bases, loss of hydrogen chloride, and high incidence of by-products. For example, in EP-A-1020435 and DE-A-1233854, tertiary amines are used as hydrogen chloride traps which precipitate out as solids in the form of the hydrochloride. Alkali metal or alkaline earth metal salts or oxides are used for this purpose in JP-A-09208589.

The aim of obtaining the purest possible hydrogen chloride and pure phosgene from a substance mixture such as is normally used in the production of isocyanates by reacting amines with phosgene is adopted in DE-A-10260084. A four-stage process is described, the essential stages of which require two separate columns and additional equipment. The process gas from the isocyanate production is composed mainly of phosgene, hydrogen chloride, solvent fractions, low-boiling compounds and inert substances (e.g., carbon monoxide and carbon dioxide). The first process step is the partial condensation of the process gas, which can take place in one or more stages, wherein depending on the equipment pressure, the procedure may be operated between 40° C. by means of cooling water and −40° C. with brine cooling. The partially condensed mixture thereby obtained is then passed, between the stripping section and the rectifying section, to the following distillation column. In the given example, using chlorobenzene as solvent, this column is designed as a bubble-cap column with 22 trays in the stripping section and 11 trays in the rectifying section. The column serves to remove hydrogen chloride from the phosgene and is equipped for this purpose with a forced circulation evaporator (Robert evaporator) and a shell-and-tube heat exchanger as head condenser. At 24.5° C. feed temperature, 38° C. bottom temperature, −9° C. head temperature and 2.5 bar head pressure, the reflux temperature of the partial condensate at the column head is −20° C. Under these conditions, the bottom product has a hydrogen chloride content of 0.01 wt. %, phosgene content of 89 wt. % and chlorine content of 10 wt. %. This stream is passed to the reaction part of the isocyanate synthesis.

As an alternative to the aforementioned evaporator in the distillation column, the removal of hydrogen chloride from the process waste gas stream to be treated may also take place by stripping from the process waste gas stream to be treated with an inert gas such as nitrogen, with the process solvent vapor, phosgene, or with another gaseous substance or substance to be evaporated.

The non-condensed fraction containing 74 wt. % of hydrogen chloride and 26 wt. % of phosgene in the head condenser of the distillation column is led at −20° C. into the lower region of an absorption column that is equipped with three sections of wire-gauze rings. Chlorobenzene at a temperature of −25° C. is added to the head of the washer, and the heat of solution of hydrogen chloride in the chlorobenzene is removed with an intermediate cooler operating at −30° C. Vapors are formed at the head of the washer, which are fed after a demister to a head condenser operating at −30° C. Here droplets are retained, which together with a small fraction of condensed vapors are returned to the bottom of this absorber or washer. The head of the column is operated at 2.2 bar and at −8° C., and the bottom at 6° C. The product removed from the head after the condenser has a hydrogen chloride content of 99.5 wt. %, a phosgene content of 0.1 wt. % and a chlorobenzene content of 0.1 wt. %. The product removed from the bottom contains 19 wt. % of phosgene, 78 wt. % of chlorobenzene and 3 wt. % of hydrogen chloride.

In the example of DE-A-10260084, the gaseous overhead extract is subsequently purified with an activated charcoal filter. The phosgene or chlorobenzene residues could not be detected by gas chromatography analysis or by IR spectroscopy.

The bottom extract from the absorber containing the aforementioned contents of phosgene and hydrogen chloride should then be passed as reflux liquid to a reaction column, to a column for the phosgene separation, or for working-up the reaction mixture. In the last case, reference is made to the possibility of saving a vapour condenser for generating the reflux liquid.

SUMMARY OF THE INVENTION

It is an object of the present invention to provide a process for the production of isocyanates and for the purification of the stream containing hydrogen chloride, phosgene and optionally solvent, low-boiling compounds and inert substances from the amine phosgenation, in a manner such that a residual concentration of phosgene in the hydrogen chloride stream of at most 0.5 wt. %, preferably at most 0.2 wt. % and most preferably at most 0.1 wt. % can be achieved. In this way, the loss of the raw material phosgene should be minimized. Safety and process problems due to high phosgene contents in the hydrogen chloride stream should thereby be avoided.

It has now been found that this and other objects which will be apparent to those skilled in the art can be achieved by an at least two-stage sequence of absorption steps and optionally condensation steps, in which at least one isothermal absorption step and at least one adiabatic absorption step are included. In this regard, the isothermal absorption may be carried out in the solvent used for the phosgenation, which may already contain amounts of phosgene, and the subsequent adiabatic absorption may likewise be carried out in the solvent used for the phosgenation. The hydrogen chloride gas can subsequently be freed from residual amounts of phosgene or solvent by partial condensation in a heat exchanger at low temperatures. The combined process thus provides a low phosgene content and low solvent content hydrogen chloride, which can be used advantageously for subsequent processes. In addition, the high degree of recovery of the phosgene that is used provides an economic advantage.

In the process according to the invention particular attention is paid to the safety aspect discussed above with respect to the prior art with regard to leakages when handling phosgene and gaseous hydrogen chloride. In the practice of the present invention, the process steps of isothermal absorption, adiabatic absorption, possible subsequent partial condensation and possible stripping can be carried out in one apparatus. By means of such an arrangement, the number of flanges and sealing surfaces, which are potential sites of leakages, can be dramatically reduced. Furthermore, the execution of the aforementioned operations is carried out in an energy-optimized embodiment in which the purity of the phosgene solution generated for the recycling can be adapted as necessary to the specific requirements of the implementation of the amine phosgenation.

DETAILED DESCRIPTION OF THE INVENTION

Figure 1:
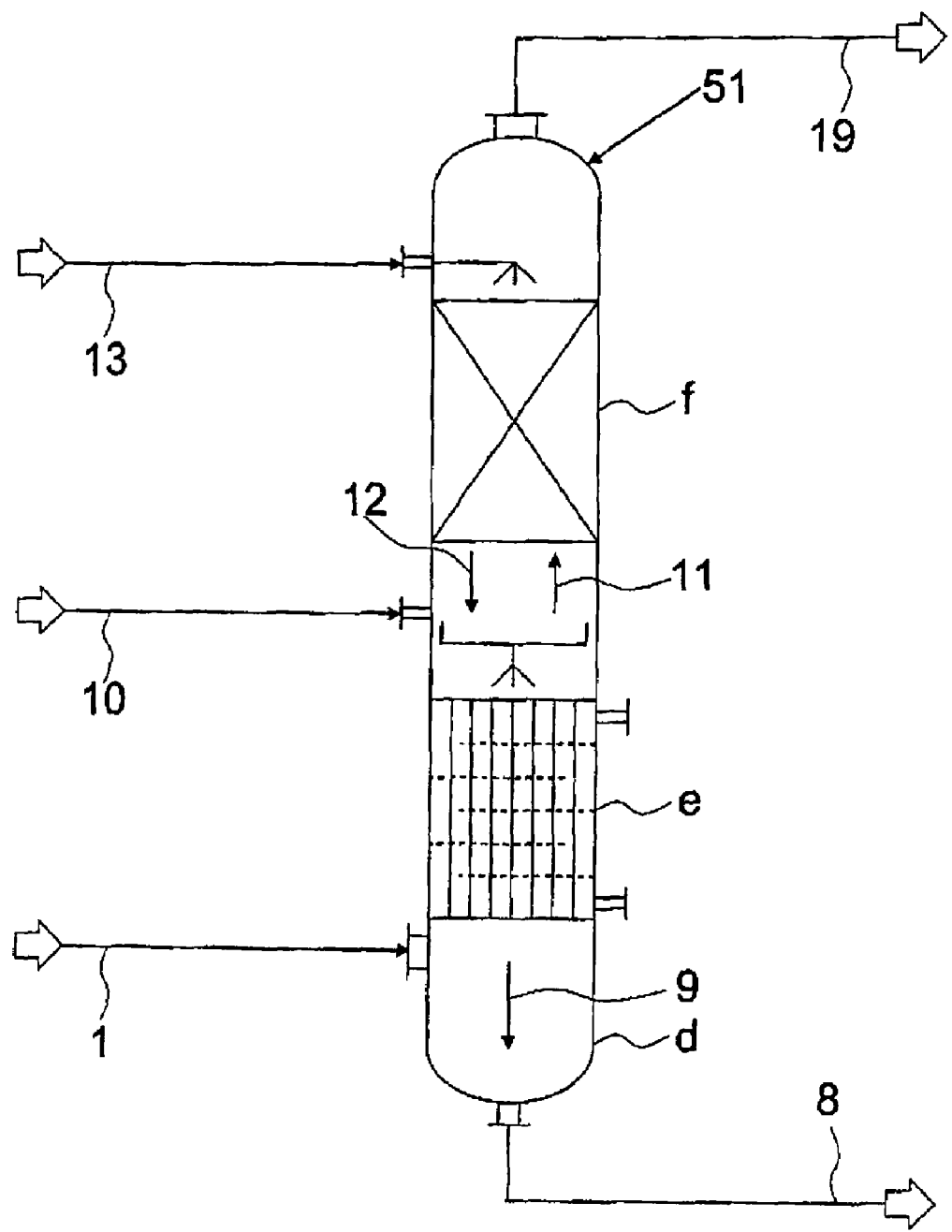
FIG. 1 is a diagrammatic representation of the separation of the stream containing hydrogen chloride, phosgene and optionally solvent, low-boiling compounds and inert substances in an absorption column.

The present invention relates to a process for the production of isocyanates, in which a) at least one amine is reacted with phosgene, optionally in the presence of a solvent, wherein the corresponding isocyanate and a stream containing hydrogen chloride, phosgene and optionally solvent, low-boiling compounds and inert substances is obtained, and b) the stream containing hydrogen chloride, phosgene and optionally solvent, low-boiling compounds and inert substances is separated in an at least two-stage sequence of absorption steps comprising at least one isothermal absorption step and at least one adiabatic absorption step, wherein a hydrogen chloride stream containing phosgene in concentrations of at most 0.5 wt. %, preferably of at most 0.2 wt. % and most preferably of at most 0.1 wt. %, based on the weight of the hydrogen chloride stream, and a liquid phosgene stream are obtained, and c) the liquid phosgene stream is then recycled to the reaction of amine with phosgene.

The reaction of amine and phosgene in step a) takes place in the liquid phase in the presence of a solvent, or in the gaseous phase. In the gaseous phase, the reaction preferably takes place in the absence of an organic solvent. The term solvent is understood in this connection to mean organic solvents such as o-dichlorobenzene, but not however inert gases such as nitrogen or materials that boil at low temperatures, such as chloroform. The inert gases are hereinafter referred to as inert substances, and the materials boiling at low temperatures (e.g., chloroform) are referred to as low-boiling compounds.

If the reaction of amine and phosgene in step a) is carried out in the liquid phase in the presence of a solvent, then as absorption agent for the isothermal absorption and for the adiabatic absorption there is preferably used the solvent that is also employed as solvent in the phosgenation in step a). The liquid phosgene stream obtained in step c) then preferably contains, apart from the solvent, also 20 to 80 wt. % of phosgene, based on the weight of the liquid phosgene stream (i.e. the mixture). This liquid phosgene stream containing solvent and phosgene can then be recycled to the reaction in step a), preferably without prior desorption of phosgene.

If the reaction of amine and phosgene in step a) is carried out in the gaseous phase, then in step c) a liquid phosgene stream is likewise obtained, preferably containing, apart from the solvent used as absorption agent, also 20 to 80 wt. % of phosgene, based on the weight of the liquid phosgene stream (i.e. the mixture). Phosgene is then separated, preferably by desorption, from this liquid phosgene stream and returned to the reaction in step a). The separated solvent (absorption agent) can be re-used in the absorption.

Preferably, the separation of the stream containing hydrogen chloride, phosgene and optionally solvent, low-boiling compounds and inert substances in step b) is carried out in such a way that first of all phosgene is partially condensed out from the stream containing hydrogen chloride, phosgene and optionally solvent, low-boiling compounds and inert substances. The resultant stream containing hydrogen chloride, phosgene and optionally solvent, low-boiling compounds and inert substances is then separated in the at least one isothermal absorption step and the at least one adiabatic absorption step.

More preferably, the vapors (substantially hydrogen chloride and possibly low-boiling compounds and inert substances) leaving the partial condensation of the phosgene from the stream containing hydrogen chloride, phosgene and optionally solvent, low-boiling compounds and inert substances is washed in co-current flow with the solvent used in the step a).

Most preferably, the isothermal absorption in the solvent used in step a) takes place in counter-current flow. Most preferably, the adiabatic absorption in the solvent used in step a) likewise takes place in counter-current flow.

Most preferably, residual solvent is condensed out in counter-current from the hydrogen chloride stream following the adiabatic absorption in the solvent used in step a). Preferably, this condensed-out solvent is then returned to the reaction in step a), optionally after purification with the liquid phosgene stream obtained in step c).

In a preferred embodiment of the present invention, the liquid phosgene-containing stream treated in accordance with step b) is first of all purified by stripping hydrogen chloride and low-boiling compounds, and is then returned to the reaction of amine with phosgene in step c).

In this connection, absorption is understood to mean the uptake and dissolution of gases and vapors in liquids. Absorption is a thermal separation process in which an auxiliary substance, the so-called wash, solution or absorption agent, is employed. The absorbate can be regenerated by desorption or stripping. The uptake of gas in the solvent (absorption agent) is generally promoted by low temperatures and high pressures, and conversely higher temperatures and lower pressures should be used in desorption. The absorption of gases in solvents (absorption agents) is an exothermic process, i.e. heat is released, which on account of the relatively poor heat transmission is transferred only to a slight extent to the gaseous phase and is mainly transferred to the liquid phase. The result of raising the temperature of the solvent (absorption agent) is, according to Henry's Law, a reduction in the absorption capacity of the solvent (absorption agent) for the substance to be dissolved. In an industrial process this at the same time means a higher solvent demand for a constant amount of absorbate. If the heat of absorption is not dissipated or is dissipated only after absorption has taken place, one speaks of adiabatic absorption. If the heat of absorption is removed uniformly during the absorption and the temperature of the solvent is at the same time maintained substantially constant, one speaks of isothermal absorption, which in practice is preferred on account of the better utilization of the solvent (absorption agent), as already described.

Preferably the adiabatic absorption takes place in fresh solvent (as absorption agent), which corresponds to the solvent used in step a). In the process according to the invention, it has been shown to be particularly advantageous to absorb the major part of the phosgene contained in the stream containing hydrogen chloride, phosgene and optionally solvent, low-boiling compounds and inert substances, optionally after partial condensation, by means of an isothermal counter-current absorption in as little solvent (absorption agent) as possible, and then to remove the still remaining residual amounts of phosgene by means of adiabatic counter-current absorption with fresh solvent (absorption agent) with only a slight adiabatic temperature rise. The optimal outflow concentration of phosgene in the vapor stream obtained from the isothermal absorption (stream containing hydrogen chloride, phosgene and optionally solvent, low-boiling compounds and inert substances) is governed in this connection by the amount of solvent (amount of absorption agent) in the adiabatic absorption and the adiabatic temperature rise that can be tolerated having regard to the absorption capacity of the solvent (absorption agent) during the course of the adiabatic absorption. Adiabatic temperature rises of from 0.1° to 20° C., preferably from 2° to 5° C. have proven to be expedient in this case.

In this connection, weight ratios of solvent to phosgene at the entry point to the isothermal absorption are preferably adjusted to from 0.1:1 to 10:1, most preferably from 1:1 to 3:1. The solvent used for the isothermal absorption may in this connection be added either completely or also in part already at the head of the adiabatic absorption.

The production of isocyanates by reacting amine with phosgene, the so-called phosgenation, takes place on an industrial scale normally in the liquid phase, wherein the phosgene and the amine can be dissolved in a solvent. Preferred solvents are: chlorinated aromatic hydrocarbons, for example chlorobenzene, o-dichlorobenzene, p-dichlorobenzene, trichlorobenzenes, the corresponding chlorotoluenes or chloroxylenes, chloroethylbenzene, monochlorodiphenyl, $\alpha$- and $\beta$-naphthyl chloride, ethyl benzoate, dialkyl esters of phthalic acid, diisodiethyl phthalate, toluene and xylenes, as well as methylene chloride, perchloroethylene, trichlorofluoromethane and butyl acetate. Mixtures of the solvents mentioned by way of example may also be used. Further examples of suitable solvents are known from the prior art. As is also known from the prior art, e.g. WO-A-96/16028, phosgene as well as the formed isocyanate itself can act as solvent. In another, preferred embodiment, the phosgenation, in particular of suitable aromatic and aliphatic diamines, takes place in the gaseous phase, i.e. above the boiling point of the amine. Gas phase phosgenation is described, for example, in EP-A-570 799. Advantages of this process compared to the otherwise conventional liquid phase phosgenation are the saving in energy, due to the minimization of a costly solvent and phosgene circulation. As a rule, solvent is also used in gas phase phosgenation, but in smaller amounts than in liquid phase phosgenation, as described, for example, in DE-A-10245704, so that here too in principle the object is to separate phosgene, hydrogen chloride and solvent.

Suitable organic amines are in principle all primary amines containing one or more primary amino groups that can react with phosgene to form one or more isocyanates containing one or more isocyanate groups. The amines contain at least one, preferably two or possibly three or more primary amino groups. Suitable organic primary amines include aliphatic, cycloaliphatic, aliphatic/aromatic, aromatic amines, diamines and/or polyamines, such as methylamine, ethylamine, butylamine, stearylamine, aniline, halogen-substituted phenylamines (e.g., 4-chlorophenylamine), 1,4-diaminobutane, 1,6-diaminohexane, 1,8-diamino-hexane, 1-amino-3,3,5-trimethyl-5-aminocyclohexane, lysine ethyl ester, lysine aminoethyl ester, 1,6,11-triaminoundecane or 1,5-naphthylenediamine, 1,4-diaminobenzene, p-xylylenediamine, perhydrogenated 2,4- and/or 2,6-diaminotoluene, 2,2'-, 2,4'-and/or 4,4'-diaminodicyclohexylmethane, 2,4-, 2,6-diaminotoluene and their mixtures, 4,4'-, 2,4'- and/or 2,2'-diphenylmethanediamine and their mixtures, as well as higher molecular weight isomeric, oligomeric or polymeric derivatives of these amines and polyamines. Other possible amines are known from the prior art. Preferred amines for the present invention are the diamines and polyamines of the diphenylmethane series (MDA, monomeric, oligomeric and polymeric amines), 2,4-, 2,6-diaminotoluene (TDA, toluoylenediamines), for example technical mixtures of 2,4-, 2,6-diaminotoluene (TDA, toluoylenediamines) in a weight ratio of 80:20, isophorone diamine and hexamethylenediamine. The corresponding isocyanates diisocyanatodiphenylmethane (MDI, monomeric, oligomeric and polymeric isocyanates), toluene diisocyanate (TDI), hexamethylene diisocyanate (HDI) and isophorone diisocyanate (IPDI) are obtained in the phosgenation.

The amines can be reacted with phosgene in a one-stage, two-stage or possibly multistage reaction. At the same time, a continuous or batchwise mode of operation is possible.

If a one-stage phosgenation in the gaseous phase is chosen, then the reaction takes place above the boiling point of the amine, preferably within a mean contact time of from 0.5 to 5 seconds and at temperatures of from 200° to 600° C.

In phosgenation in the liquid phase, temperatures of from 20° to 240° C. and pressures of from 1 to ca. 50 bar absolute are normally used. Phosgenation in the liquid phase may be carried out as a one-stage or multistage process, in which phosgene can be used in stoichiometric excess. The amine solution and the phosgene solution are combined preferably using a static mixing element and are then fed, for example, from below upwardly through one or more reaction towers, where the mixture reacts completely to form the desired isocyanate. In addition to reaction towers that are provided with suitable mixing elements, reaction vessels equipped with a stirring device may also be used. Static mixing elements or special dynamic mixing elements may be employed. Suitable static and dynamic mixing elements are known from the prior art.

As a rule, the continuous liquid phase production of isocyanates on an industrial scale is carried out in two stages. In the first stage which is generally conducted at temperatures of at most 220° C., preferably at most 160° C., carbamoyl chloride is formed from amine and phosgene and amine hydrochloride is formed from amine and hydrogen chloride that has split off. This first stage is highly exothermic. In the second stage, the carbamoyl chloride is cleaved to form isocyanate and hydrogen chloride and the amine hydrochloride is reacted to form carbamoyl chloride. The second stage is generally carried out at temperatures of at least 90° C., preferably from 100° to 240° C.

After the amine phosgenation, the isocyanates formed in the phosgenation are generally separated from the reaction mixture. This is carried out, for example, by first separating the phosgenation reaction mixture into a liquid product stream and a gaseous product stream in a manner known to the person skilled in the art.

Relevant processes are described, for example, in U.S. Pat. No. 3,544,611 and GB-A-827376. The liquid product stream contains essentially the isocyanate or isocyanate mixture, solvent that may have been used, as well as a small proportion of unreacted phosgene. The gaseous product stream is composed substantially of hydrogen chloride gas, excess phosgene, possibly minor amounts of solvent, as well as secondary products from the phosgene production, such as carbon dioxide. The further working-up of the liquid product stream may result in a further separation of residual amounts of phosgene.

As complete a recovery of excess phosgene as possible for re-use in the phosgenation as well as the isolation of hydrogen chloride that is as pure as possible for further utilization is therefore desired, particularly for economic reasons.

The stream containing hydrogen chloride, phosgene and optionally solvent, low-boiling compounds and inert substances, which normally occurs in the reaction of aliphatic or aromatic amines with phosgene in the liquid phase to form the corresponding isocyanates in step a), preferably contains from 20 to 75 wt. % of phosgene, from 5 to 50 wt. % of solvent and from 5 to 50 wt. % of hydrogen chloride. The breadth of these ranges for the composition of the stream containing hydrogen chloride, phosgene and optionally solvent, low-boiling compounds and inert substances is due to the number of different possible processes for the phosgenation which are characterised by different pressures, temperatures and process solvents, and that can optionally take place in the gaseous phase or free of solvent.

The stream containing hydrogen chloride, phosgene and optionally solvent, low-boiling compounds and inert substances, which normally occurs in the reaction of aliphatic or aromatic amines with phosgene in the gaseous phase to form the corresponding isocyanates in step a), preferably contains from 20 to 50 wt. % of solvent, from 30 to 40 wt. % of phosgene, from 10 to 50 wt. % of hydrogen chloride and less than 1 wt. % of low-boiling compounds and inert substances.

The heat of absorption produced in the isothermal absorption of the phosgene in the wash liquid is dissipated indirectly via a heat exchange surface uniformly and already during its production to a suitable cooling medium with an initial temperature of preferably −40° to 0° C., most preferably −25° to −15° C., whereby the temperature of the absorption agent is maintained constant at a correspondingly low value. In this way it is possible, despite the unfavorable temperature dependence of the distribution coefficient on the absorbate in the absorbent, to achieve a high phosgene dissolution capacity of the absorption agent and thereby a particularly economical demand for absorption agent.

The isothermal absorption is preferably carried out in the process according to the invention with a falling film absorber as apparatus (e.g., as illustrated in FIG. 1). Shell-and-tube heat exchangers, preferably vertically arranged, single flight shell-and-tube heat exchangers are normally used for this purpose. The absorption agent and the charged vapors may be led both inside as well as outside the tubes, in co-current or counter-current to the cooling medium, which is correspondingly situated on the other side of the tube wall. The absorption agent and the charged vapors are, however, preferably guided within the tubes in counter-current and the coolant is preferably guided outside the tubes. Due to the relatively large concentration differences between charged vapors and absorbent the wash liquid, consumption can drop with the counter-current mode of operation. The tube diameter may be from 10 to 200 mm, preferably from 40 to 100 mm, most preferably from 50 to 70 mm. The tube length is normally between 1 and 10 m, preferably between 3 and 8 m, most preferably between 5 and 7 m. The number of tubes varies in a technically feasible scale from 100 to 3000, preferably from 600 to 1800. The tubes may optionally be provided with filling materials, packings or other internal fittings corresponding to the prior art and known to the person skilled in the art, in order to provide as large a material exchange surface as possible and as large a material transfer coefficient as possible between the vapors and the absorption agent. These may be conventional types of packings for absorption, such as for example B1, C1 (Montz) or Mellapak, Kerapak (Sulzer) or Ralupak (Raschig) or Rombopak (Kühni) or also all other conventional types of packing for rectification purposes or types of filling materials (all specially identified by VFF), such as e.g. Raschig rings, Pall rings, or saddles of the Intalox, Berl, Super-Torus (Raschig) or Super, Interpack, Top-Pak, Hacketten, Igel, VSP or Hiflow-Ring type (Rauschert) in the commercially available sizes and made of materials known to the person skilled in the art that are resistant under the prevailing conditions to the substances in the system. In addition, internal fittings such as static mixers, e.g. of the SMV type from Koch-Glitsch, or also flow turbulators, e.g. of the Hi-Tran type from Cal Gavin, may also be used. Filling materials are most preferably employed.

The purified phosgene solution (the liquid phosgene stream) removed from the isothermal absorption may (optionally after further working-up or after desorption of the phosgene) be returned to the reaction part of the isocyanate synthesis. Depending on the size of the plant for the isocyanate production, the freshly-produced, gaseous phosgene can either be condensed together with the vapor stream from the phosgenation in the absorber and dissolved, or condensed in a separate phosgene condensation within the phosgene production and led separately into the reaction part. The temperature of the vapors at the outlet of the isothermal absorption is preferably in the range between 10° and −20° C., more preferably between 0° and −20° C., most preferably between −5° and −15° C. The vapors from the isothermal absorption, which still contain only a minor amount of phosgene, are then preferably washed in the adiabatic absorption in counter-current with cold process solvent in order to remove phosgene and possibly other components, such as low-boiling compounds, that are soluble in the absorption agent from the vapor stream. The function of the cold process solvent may preferably be effected via a liquid distributor corresponding to the prior art. For the adiabatic absorption trays, filling materials or packings may be used for the exchange material. Structured packings, e.g. of the Mellapak type (Sulzer) are most preferably employed for this purpose. The purified hydrogen chloride stream is then preferably removed at the head of the absorption column, which in a preferred embodiment of the present invention includes the process stages of isothermal and adiabatic absorption.

Due to the particularly advantageous combination of isothermal and adiabatic absorption in the sequence described above (preferably in an apparatus) it is possible, compared to purely adiabatic absorption, to absorb the phosgene efficiently using only a small amount of process solvent. In addition, the externally arranged heat exchangers, which can present a safety problem and are required as intermediate coolers in purely adiabatic absorption in order to remove the heat of absorption, are avoided. The layout of the two absorption steps, known to the person skilled in the art, is implemented according to the principle of isothermally absorbing so much phosgene that in the adiabatic absorption the temperature increase of the absorption agent is still tolerable with respect to the phosgene solubility.

The head temperature of the absorption column in the preferred combination of isothermal and adiabatic absorption in one apparatus is preferably from −40° to 0° C., most preferably from −30° to −20° C. The head pressure is preferably between 1 and 35 bar absolute, most preferably between 1.2 and 3 bar absolute.

The invention is described in more detail hereinafter with the aid of the drawings.

FIG. 1 is a diagrammatic representation of the separation of the stream containing hydrogen chloride, phosgene and optionally solvent, low-boiling compounds and inert substances in an absorption column.

Stream 1 containing hydrogen chloride, phosgene and optionally solvent, low-boiling compounds and inert substances, which normally occurs in the reaction of aliphatic or aromatic amines with phosgene to form the corresponding isocyanates is, in a special embodiment of the invention for the separation, introduced directly into an absorption column 51, shown diagrammatically in FIG. 1, underneath the isothermal absorption stage e. At the head of the isothermal absorption column e the liquid outflow 12 from the adiabatic absorption stage f as well as possibly solvent partially charged with phosgene and hydrogen chloride (stream 10), which originates from the vacuum system or from the solvent separation of the isocyanate synthesis, is optionally cooled, and is added as absorption agent via a liquid distributor in counter-current to the gaseous fraction of the substance mixture stream 1.

The absorbate 9 from the isothermal absorption stage e is passed to the bottom d of the absorption column 51. The purified phosgene solution 8 (the liquid phosgene stream) may be returned to the reaction part of the isocyanate synthesis. Depending on the size of the plant for the isocyanate production, the freshly-produced, gaseous phosgene can either be condensed together with the vapor stream from the phosgenation in the absorber and dissolved, or condensed in a separate phosgene condensation within the phosgene production and led separately into the reaction part. The temperature of the vapors at the outlet of the isothermal absorption is preferably in the range between 10° and −20° C., more preferably between 0° and −20° C., most preferably between −5° and −15° C. The vapors 11 from the isothermal absorption e, which will still contain only a minor amount of phosgene, are then washed in the adiabatic absorption stage f in counter-current with cold process solvent 13 in order largely to free the vapor stream 11 from phosgene and possibly from other components, such as low-boiling compounds, that are soluble in the absorption agent. The function of the cold process solvent 13 is performed by a liquid distributor corresponding to the prior art. For the adiabatic absorption trays, filling materials or packings may be used for the material exchange, structured packings, e.g. of the Mellapak type (Sulzer), most preferably being employed for this purpose. The purified hydrogen chloride stream 19 is then removed at the head of the absorption column 51, which in this embodiment includes the process stages of isothermal and adiabatic absorption.

Figure 2:
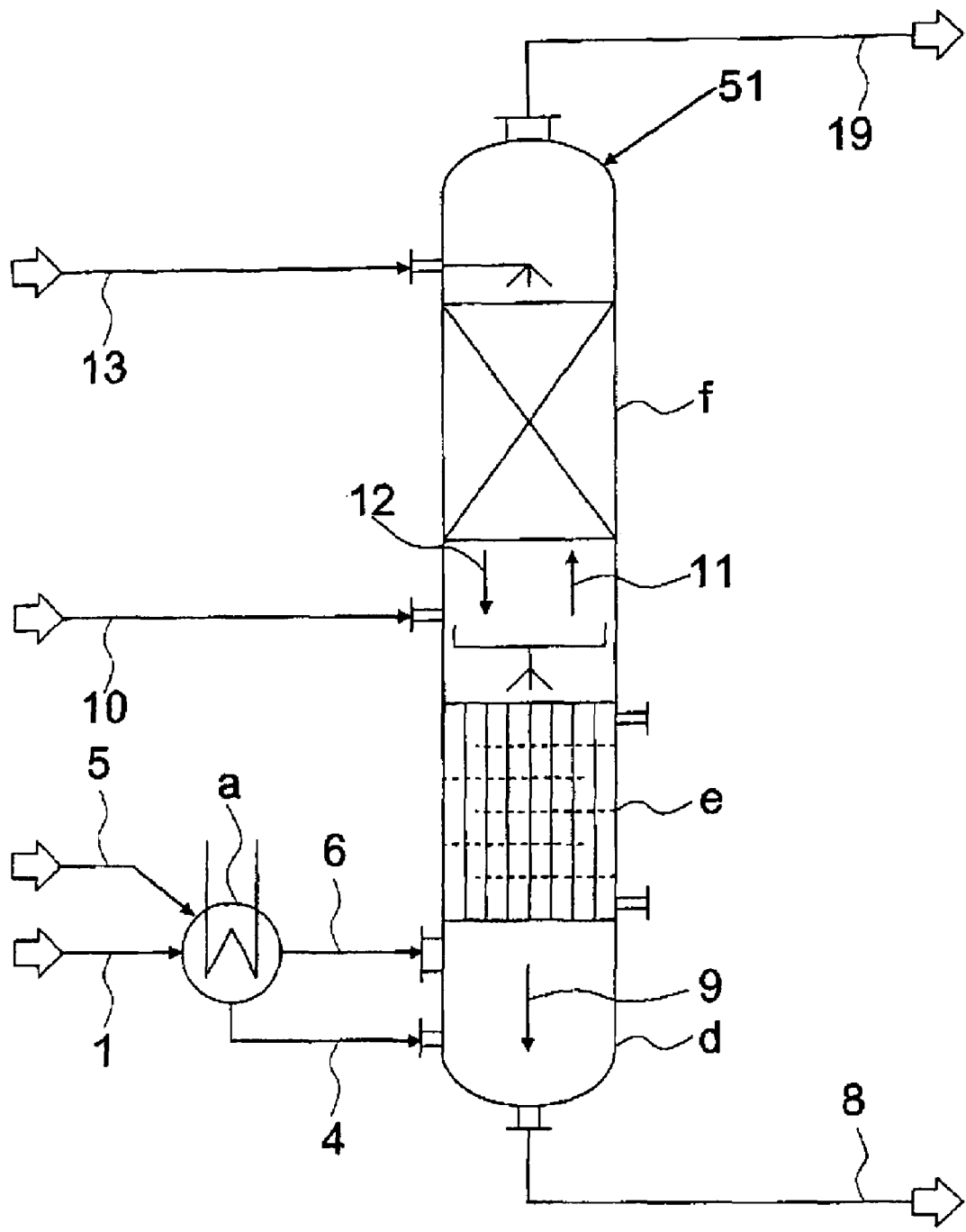
FIG. 2 is a diagrammatic representation of the separation of the stream containing hydrogen chloride, phosgene and optionally solvent, low-boiling compounds and inert substances in an absorption column with partial phosgene condensation upstream.

FIG. 2 is a diagrammatic illustration of the separation of the stream containing hydrogen chloride, phosgene and optionally solvent, low-boiling compounds and inert substances in an absorption column with partial phosgene condensation upstream.

In the embodiment illustrated in FIG. 2, as much phosgene as possible is separated as condensate by partial condensation in a heat exchanger (condenser a) from the stream 1 containing hydrogen chloride, phosgene and optionally solvent, low-boiling compounds and inert substances occurring in the reaction of aliphatic or aromatic amines with phosgene to form the corresponding isocyanates, before the already-described combination of isothermal and adiabatic absorption (shown in FIG. 1).

All condensers corresponding to the prior art are suitable as heat exchangers. In order to save expensive cooling energy for cold brine, instead of a one-stage process in which the substance mixture stream 1 is also cooled by means of cold brine, a two-stage or possibly multistage process may be employed. The number of stages for the partial condensation and cooling and their temperatures may vary depending on local factors.

The condensation step is preferably carried out with cold brine at a temperature of preferably from −40° to −0° C., most preferably at −20° to −10° C. The condensation step may, as illustrated in FIG. 2, be carried out under the addition of solvent weakly charged with phosgene (i.e. less than 1 wt. %, preferably below 0.5 wt. % based on the weight of the mixture) and hydrogen chloride, originating from the ring liquid system of the vacuum pumps or from the solvent separation of the isocyanate synthesis or from an arbitrary mixture of both streams (stream 5), together with stream 1 containing hydrogen chloride, phosgene and optionally solvent, low-boiling compounds and inert substances. The condensation step with cold brine is preferably preceded by a condensation step with air-cooled cold brine, at preferably from 25° to 50° C., most preferably at 30° to 40° C., and optionally in addition by a cooling step with warmer cold brine at preferably 0° to 25° C. (not shown in FIG. 2).

The absorption of the phosgene from the substance stream 6 that is obtained from the partial condensation in the condenser a, takes place similarly to the process illustrated in FIG. 1. The condensate stream 4 from the partial condensation in the condenser a is led to the bottom d of the absorption column 51 and may be returned, together with the absorbate, as phosgene solution 8 to the reaction part of the isocyanate synthesis. Depending on the size of the plant for the isocyanate production, the freshly-produced, gaseous phosgene can either be condensed together with the vapor stream from the phosgenation in the absorber and dissolved, or condensed in a separate phosgene condensation within the phosgene production and led separately into the reaction part. Due to the upstream connection of a one-stage or multistage partial condensation, the necessary amounts of absorption agent can be reduced and in this way the circulating streams for the process solvent are minimized, and accordingly the energy consumption in the isocyanate synthesis is reduced. In addition, the size of the falling film absorber is reduced by having one or more condensation steps.

Figure 3:
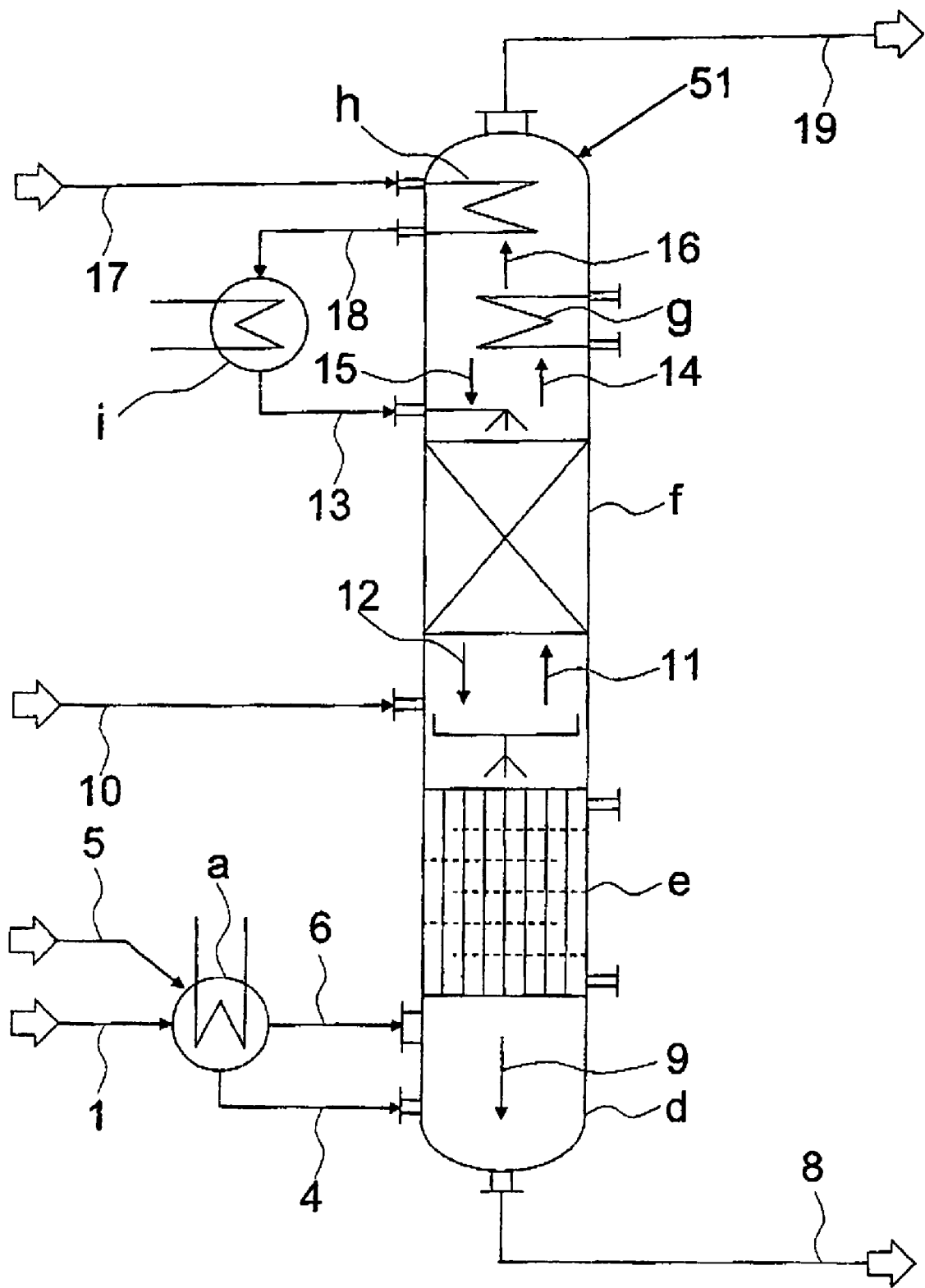
FIG. 3 is a diagrammatic representation of the separation of the stream containing hydrogen chloride, phosgene and optionally solvent, low-boiling compounds and inert substances in an absorption column with partial phosgene condensation upstream and supercooling of solvent that is still contained from the gaseous head stream of the absorption column.

FIG. 3 is a diagrammatic illustration of the separation of the stream containing hydrogen chloride, phosgene and optionally solvent, low-boiling compounds and inert substances in an absorption column with upstream-connected partial phosgene condensation and supercooling of solvent still contained from the gaseous head stream of the absorption column.

In the embodiment illustrated in FIG. 3, phosgene is separated from stream 1 containing hydrogen chloride, phosgene and optionally solvent, low-boiling compounds and inert substances occurring in the reaction of aliphatic or aromatic amines with phosgene to form the corresponding isocyanates, wherein by way of amplification of the embodiment illustrated in FIG. 2 (combination of partial condensation of phosgene as well as isothermal and adiabatic absorption of phosgene), solvent still contained from the gaseous head stream of the absorption column is separated by supercooling in a heat exchanger and the cooling energy is then recovered at the head of the column via a suitable attachment.

Stream 1 containing hydrogen chloride, phosgene and optionally solvent, low-boiling compounds and inert substances is, as already illustrated in FIG. 2, first of all partially separated by partial condensation followed by isothermal and adiabatic absorption.

The vapors 14 from the adiabatic absorption stage f are highly supercooled once more in the post-condenser g, and solvent that is still present is partially condensed and added as liquid reflux 15 to the adiabatic absorption stage f. The non-condensable fractions 16 are fed through a heat exchanger h to recover energy and there cool the process solvent stream 17, which is then led as pre-cooled stream 18 into the one-stage or multistage heat exchanger i for further cooling and is next added as stream 13, together with the liquid reflux 15, as absorption agent at the head of the adiabatic absorption stage f. The purified hydrogen chloride stream 19 is removed in gaseous form at the heat exchanger h, which at the same time forms the head of the absorption column, the said column including the steps of isothermal absorption, adiabatic absorption, post-condensation and energy recovery. All heat exchangers corresponding to the prior art are suitable as heat exchangers for the post-condensation and energy recovery, shell-and-tube heat exchangers preferably being used and shell-and-tube heat exchangers with crosscurrent-countercurrent switching most preferably being used, which are directly incorporated into the head of the absorption column. The gas flows from the top downwards transversely and in counter-current to the tubes through which brine flows.

The head temperature of the absorption column 51 is, by use of the energy saving arrangement, preferably from −20° to 40° C., most preferably from −10° to 20° C. The head pressure is preferably between 1 and 35 bar absolute, particularly preferably between 1.2 and 3 bar absolute. The temperature of the gas stream between the post-condenser and energy recovery is preferably between −40° and −10° C., most preferably between −40° and −25° C.

Figure 4:
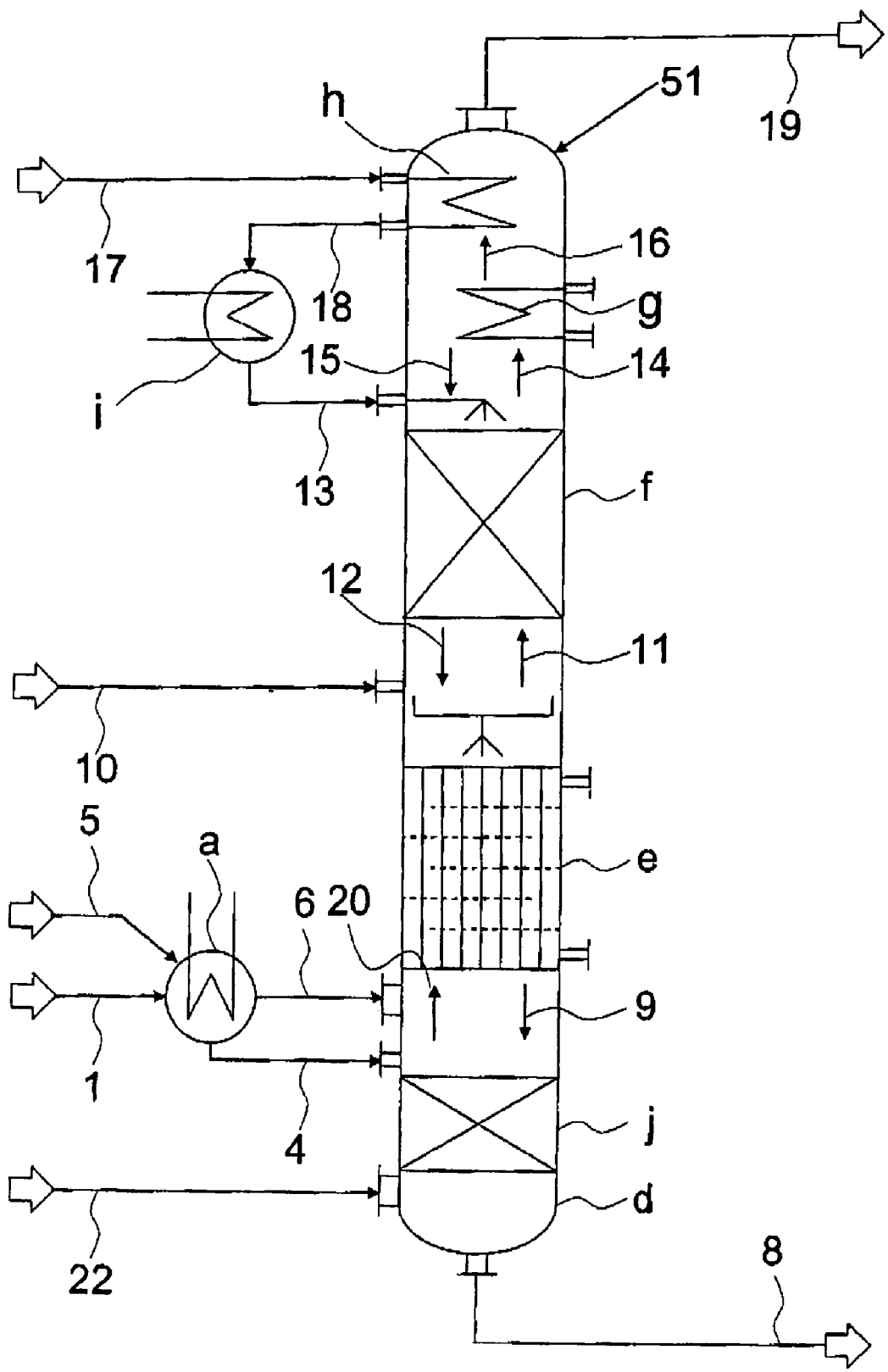
FIG. 4 is a diagrammatic representation of the separation of the stream containing hydrogen chloride, phosgene and optionally solvent, low-boiling compounds and inert substances in an absorption column with partial phosgene condensation upstream and supercooling of solvent that is still contained from the gaseous head stream of the absorption column as well as stripping of the phosgene solution.

FIG. 4 shows diagrammatically the separation of the stream containing hydrogen chloride, phosgene and optionally solvent, low-boiling compounds and inert substances in an absorption column with upstream partial phosgene condensation and supercooling of solvent that is still contained from the gaseous head stream of the absorption column, as well as stripping of the phosgene solution.

In the embodiment illustrated in FIG. 4, the purity of the liquid phosgene stream 8 (phosgene solution) that is removed at the bottom of the absorption column 51 can be increased once more, particularly with respect to the low-boiling compounds that are soluble in phosgene and/or in the solvent, such as for example hydrogen chloride. Since in the embodiment illustrated in FIG. 4 additional substance streams are formed within the absorption column compared to the embodiments shown in FIGS. 1, 2 and 3, the process according to FIG. 4 will be described once more in detail hereinafter.

Stream 1 containing hydrogen chloride, phosgene and optionally solvent, low-boiling compounds and inert substances that normally occurs in the reaction of aliphatic or aromatic amines with phosgene to form the corresponding isocyanates is partially condensed, optionally together with a solvent stream 5 slightly charged with phosgene (i.e., less than 1 wt. %, preferably below 0.5 wt. % based on the weight of the mixture) and hydrogen chloride, first of all in a first heat exchanger a at temperatures of preferably 25° to 50° C., most preferably 30° to 40° C., and cooled. The cooled substance mixture thereby obtained is then preferably partially condensed in a second heat exchanger (not shown in FIG. 4), again at temperatures of preferably 0° to 25° C., most preferably 5° to 15° C., and cooled. The condensate 4 is added to the head of the stripping section j. The uncondensed fraction may preferably be partially condensed (not shown in FIG. 4) by means of an additional heat exchanger and under the addition of solvent slightly charged with phosgene (i.e. less than 1 wt. %, preferably below 0.5 wt. % based on the weight of the mixture) and hydrogen chloride, originating from the ring liquid system of the vacuum pumps or from the solvent separation of the isocyanate synthesis or from an arbitrary mixture of both streams (stream 5), at temperatures of preferably −40° to 0° C., particularly preferably at −10° to −20° C. and cooled. The condensate that is thereby obtained may similarly be added to the head of the stripping section j.

The uncondensed vapors 6 still containing large amounts of phosgene, as well as the vapors 20 from the stripping section j of the phosgene solution, are added to the foot of the isothermal absorption stage e. The heat of absorption that is produced is immediately released to a cooling medium. The liquid outflow 12 from the adiabatic absorption stage f as well as solvent possibly partially charged with phosgene and hydrogen chloride (stream 10), originating from the vacuum system or from the solvent separation of the isocyanate synthesis, is optionally cooled at the head of the isothermal absorption stage e and is added as absorption agent via a liquid distributor in counter-current to the uncondensed vapors 6 and 20.

The charged solvent 9 from the isothermal absorption stage f as well as the condensate 4 from the partial condensation in the condenser a, which depending on the solubility is still charged with certain amounts of low-boiling compounds, are added to the head of the stripping section j and are there stripped in counter-current with the vapor stream 22. The vapor stream 22 is preferably composed for the most part of phosgene and the normal impurities in phosgene production, such as hydrogen, oxygen, traces of hydrogen chloride, carbon monoxide, carbon dioxide, etc. The stripped phosgene solution runs into the bottom d of the absorption column 51. There a phosgene solution 8 largely freed from hydrogen chloride (liquid phosgene stream) is removed, and can be returned to the reaction part of the isocyanate synthesis. Depending on the size of the plant for the isocyanate production, the freshly-produced, gaseous phosgene can either be condensed together with the vapor stream from the phosgenation in the absorber and dissolved, or condensed in a separate phosgene condensation within the phosgene production and led separately into the reaction part. Depending on the requirements for purity of the phosgene solution, the condensate stream 4 from the partial condensation in the condenser a may also be passed directly to the bottom d of the absorption column 51. The proportion of hydrogen chloride and other low-boiling compounds is thereby increased somewhat.

The implementation of the stripping section j corresponds to the known prior art. The design is executed having regard to the desired content of low-boiling compounds in the bottom stream, in a manner and way known to the person skilled in the art and conventionally employed for such separations. The apparatus may include a packing section, filling material section or tray column section.

The integration of the separation of low-boiling compounds in the absorption column while saving on additional heat exchangers arranged outside the column and the heating and/or cooling energy that otherwise has to be supplied separately achieved by the process of the present invention is particularly advantageous with respect to investment and operating costs and also safety. It is however also possible to produce the vapor stream 22 for the stripping of the phosgene solution in a heat exchanger arranged outside or possibly inside, through the evaporation of part of the phosgene solution 8 (liquid phosgene stream) leaving the bottom d of the absorption column 51.

The remaining vapors 11 from the isothermal absorption stage e only still containing a small amount of phosgene are fed in at the foot of the adiabatic absorption stage f. Cold solvent 13 and the condensate 15 flowing out from the subsequent post-condensation g are added in counter-current to this feed at the head of the adiabatic absorption stage f.

The vapors 14 from the adiabatic absorption stage f are strongly cooled once more in the post-condenser g, and phosgene still present and process solvent are partially or completely condensed and added as liquid reflux 15 to the adiabatic absorption stage f. The non-condensable fractions 16 are led through a heat exchanger h for energy recovery and there partially cool the solvent stream 17, which is then led as a pre-cooled stream 18 into the one-stage or multistage heat exchanger i for further cooling, and is next added as stream 13, together with the liquid reflux 15, as absorption agent at the head of the adiabatic absorption stage f. The purified hydrogen chloride stream 19 is removed in gaseous form at the heat exchanger h, which at the same time forms the head of the absorption column, which includes the steps of stripping, isothermal absorption, adiabatic absorption, post-condensation and energy recovery.

The head temperature of the absorption column in energy saving mode is preferably −20° to 40° C., most preferably −10° to 20° C. The head pressure is preferably between 1 and 35 bar absolute, most preferably between 1.2 and 3 bar absolute.

Traces of solvent, low-boiling compounds and phosgene that are still present may be removed from the hydrogen chloride stream containing phosgene and solvent by post-purification by means of adsorption, for example on activated charcoal, or by other suitable methods, such as for example one-stage or multistage condensing out or freezing out at very low temperatures, depending on the fixed point of the process solvent that is used and the selected pressure, or by a distillation of the condensed hydrogen chloride. The highly pure hydrogen chloride that is thereby obtained may then be used for production of ethylene dichloride (vinyl chloride), in a Deacon process, or for electrolysis of hydrogen chloride.

Due to the particularly advantageous combination of isothermal and adiabatic absorption it is possible, in contrast to purely adiabatic absorption, to absorb the phosgene particularly efficiently with only a small amount of solvent. This constitutes a further step in minimizing the energy-intensive solvent circulations employed in large-scale isocyanate synthesis.

In the embodiment of the present invention illustrated in FIG. 4, the concentration of hydrogen chloride and other low-boiling compounds in the phosgene solution (liquid phosgene stream) can be reduced still further, if necessary by a stripping part in the absorption column, below the isothermal absorption, without needing an extra separate column with bottom evaporator and head condenser, by using a vapor stream from the phosgene production of the isocyanate synthesis as stripping gas and condensing the stream during the stripping. Normally this vapor stream in the isocyanate synthesis is liquefied in a separate condensation and then added to the phosgene solution. In the process according to the invention, the condensation is optionally effected by means of the latent heat of the phosgene solution flowing from the isothermal absorption.

A further advantage of the process of the present invention in comparison to processes that employ both a purely adiabatic absorption and a prior distillation to reduce the hydrogen chloride concentration in the phosgene solution, is the markedly lower cooling energy consumption of cooling brine, since the combined absorption, in particular the effective combination of isothermal and adiabatic absorption with stripping by phosgene vapors, does not require additional evaporation energy and therefore no additional condensation energy. The energy used to condense phosgene vapors employed for the stripping is saved in the phosgene production for the isocyanate synthesis.

With regard to the safety aspect of the process of the present invention, when handling phosgene, it is particularly advantageous to carry out the isothermal and adiabatic absorption, as well as the optionally subsequent post-condensation followed by energy recovery and optionally the stripping of the phosgene solution, preferably in a single piece of apparatus, for example in a column body, since in this way the possibility of leaks is reduced by minimizing the number of externally-located pipeline flange connections.

EXAMPLE

The separation of a stream containing hydrogen chloride, phosgene and optionally solvent, low-boiling compounds and inert substances that normally occurs in the reaction of aliphatic or aromatic amines with phosgene to form the corresponding isocyanates is effected by a three-stage partial condensation, in which in the third stage chlorobenzene is additionally added in co-current, followed by partial isothermal absorption of the phosgene with chlorobenzene in counter-current, followed by an adiabatic absorption of the remaining phosgene with chlorobenzene in counter-current, and finally by a post-condensation of the residual chlorobenzene from the hydrogen chloride stream containing small amounts of phosgene and solvent as illustrated in FIG. 4.

The phosgene solution formed at the bottom of the absorption column, together with the condensates from the partial condensation, is then partially freed from hydrogen chloride by stripping with a gaseous phosgene stream from the phosgene production, corresponding to FIG. 4.

A hydrogen chloride stream 1 of 39.2 kg/hour is employed for the partial condensation in the three successive heat exchangers operating at 45° C. (air cooling) +10° C. (cooling brine) and −17° C. (cooling brine). The hydrogen chloride stream that is used contains 25.3 wt. % of hydrogen chloride, 42.3 wt. % of chlorobenzene, 32.4 wt. % of phosgene and minor amounts of low-boiling compounds typical for an isocyanate synthesis. In the last condensation step at the lowest temperature, an additional 0.53 kg/hour of chlorobenzene is added in co-current in order to improve the condensation performance. The liquid condensates 4 from the second and third stages are added directly to the stripping part. The waste gases 6 from the third stage are fed into the isothermal absorption.

The following combination of isothermal and adiabatic absorption with post-condensation of the solvent from the waste gas and stripping of the low-boiling compounds from the phosgene solution takes place in this example in a combination of several apparatuses, which were connected as if the implemented steps had been arranged within one column body.

A vertically arranged heat exchanger with a tube was used for the isothermal absorption. The cooling was carried out with cooling brine at −17° C. The tube had a diameter of 54.4 mm, a length of 3 m and was filled with Pall rings of size 15×15 mm. The waste gas stream 6 from the partial condensation was added at a rate of 13.4 kg/hour and at a temperature of −10° C. to the lower end of the heat exchanger. The composition of this waste gas was ca. 69.28 wt. % of hydrogen chloride, 0.04 wt. % of chlorobenzene, 30.68 wt. % of phosgene and traces of low-boiling compounds typical of an isocyanate synthesis. The feed at the head of the isothermal absorption was composed of 2.1 kg/hour of chlorobenzene slightly charged with phosgene (2.6 wt. % of phosgene) and the 7.56 kg/hour outflow from the adiabatic absorption 12 (4.8 wt. % of hydrogen chloride, 93.9 wt. % of chlorine and 1.3 wt. % of phosgene). The hydrogen chloride stream 11 of 9.92 kg/hour pre-purified by the isothermal absorption and having a composition of 98.1 wt. % of hydrogen chloride, 0.2 wt. % of chlorobenzene, 1.0 wt. % of phosgene and 0.7 wt. % of the low-boiling compounds typical for an isocyanate synthesis was fed to the adiabatic absorption stage, and the outflowing phosgene solution 9 was fed to the stripping part.

The adiabatic absorption is carried out in a packing column with a diameter of 55 mm. The packing height was 1 m. For the absorption, 7.08 kg/hour of chlorobenzene 13 at −35° C. and the condensate stream 15 of 0.012 kg/hour from the post-condensation were added in counter-current to the head of the adiabatic absorption. The hydrogen chloride stream 14 of 9.45 kg/hour leaving the adiabatic absorption and freed from phosgene was composed of 99.1 wt. % of hydrogen chloride, 0.14 wt. % of chlorobenzene, 0.03 wt. % of phosgene and 0.73 wt. % of the low-boiling compounds typical of an isocyanate synthesis. This stream was very largely freed in the following post-condensation at −35° C. also from residual amounts of solvent. 9.44 kg/hour of industrial hydrogen chloride 16 were obtained, with a composition of 99.21 wt. % of hydrogen chloride, 0.03 wt. % of chlorobenzene, 0.03 wt. % of phosgene and 0.73 wt. % of the low-boiling compounds typical for an isocyanate synthesis. The head pressure was 2.5 bar absolute and the head temperature is −35° C.

The outflowing phosgene solution from the partial condensation 4 was added together with the one from the isothermal absorption 9 to the head of the stripping column. The 40.52 kg/hour phosgene solution with a composition of 2.9 wt. % of hydrogen chloride, 64.7 wt. % of chlorobenzene and 32.4 wt. % of phosgene was stripped in counter-current by 1.39 kg/hour of the gaseous phosgene stream 22 from the phosgene production. A packing column with a diameter of 25 mm was used as stripping column, the packing height was 0.2 m. The outflowing phosgene solution 8 had a composition of 1.4 wt. % of hydrogen chloride, 64.2 wt. % of chlorobenzene, 34.4 wt. % of phosgene and a stream flow rate of 40.84 kg/hour.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate comprising:
   a) reacting at least one amine with phosgene, optionally in the presence of a solvent, to produce a corresponding isocyanate and a stream containing hydrogen chloride, phosgene and optionally solvent, low-boiling compounds and inert substances,
   b) separating the stream containing hydrogen chloride, phosgene and optionally solvent, low-boiling compounds and inert substances in an at least two-stage sequence of absorption steps comprising (1) at least one isothermal absorption step and (2) at least one adiabatic absorption step to obtain (i) a hydrogen chloride stream containing no more than 0.5 wt. % phosgene, based on total weight of the hydrogen chloride stream and (ii) a liquid phosgene stream, and
   c) recycling the liquid phosgene stream (ii) to step a).

2. The process of claim 1 in which the reaction in step a) is carried out in the gaseous phase.

3. The process of claim 2 in which the liquid phosgene stream (ii) contains from 20 to 80 wt. % of phosgene, based on total weight of the liquid phosgene stream.

4. The process of claim 2 in which phosgene is separated by desorption from the liquid phosgene stream (ii) and the separated phosgene is used in step a).

5. The process of claim 1 in which the reaction in step a) is carried out in the liquid phase in the presence of a solvent.

6. The process of claim 5 in which the solvent used in step a) is used in step b) as an absorption agent in the at least one isothermal absorption step and the at least one adiabatic absorption step.

7. The process of claim 6 in which the liquid phosgene stream (ii) contains from 20 to 80 wt. % of phosgene, based on total weight of the liquid phosgene stream.

8. The process of claim 7 in which the liquid phosgene stream (ii) is used in step a).

9. The process of claim 5 in which phosgene is partially condensed out from the stream containing hydrogen chloride, phosgene and optionally solvent, low-boiling compounds and inert substances before separation in the at least two-stage sequence of absorption steps.

10. The process of claim 9 in which vapors from the partial condensation of the phosgene are washed in co-current with the solvent used in step a).

11. The process of claim 5 in which the isothermal absorption (1) and the adiabatic absorption (2) are carried out in counter-current.

12. The process of claim 5 in which the hydrogen chloride stream (i) is used in step a).

13. The process of claim 1 in which the liquid phosgene stream (ii) is purified by stripping hydrogen chloride and low-boiling compounds from the liquid phosgene stream (ii) and the purified phosgene stream is used in step a).

* * * * *